(12) United States Patent
Pan et al.

(10) Patent No.: US 9,898,913 B2
(45) Date of Patent: Feb. 20, 2018

(54) MEDICAL ALERT MESSAGE PRE-CONFIGURATION AND MISSION HANDLING METHOD

(71) Applicant: EBM TECHNOLOGIES INCORPORATED, Taipei (TW)

(72) Inventors: William Pan, Taipei (TW); Cheng-Yuan Hsu, New Taipei (TW)

(73) Assignee: EBM TECHNOLOGIES INCORPORATED, Taipei (TW)

( * ) Notice: Subject to any disclaimer, the term of this patent is extended or adjusted under 35 U.S.C. 154(b) by 0 days.

(21) Appl. No.: 15/186,550

(22) Filed: Jun. 20, 2016

(65) Prior Publication Data

US 2017/0178482 A1 Jun. 22, 2017

Related U.S. Application Data

(66) Substitute for application No. 62/270,045, filed on Dec. 21, 2015.

(30) Foreign Application Priority Data

Mar. 30, 2016 (TW) ................. 105109969

(51) Int. Cl.
*G08B 21/02* (2006.01)
*G06Q 10/06* (2012.01)
*A61B 5/00* (2006.01)

(52) U.S. Cl.
CPC ............ *G08B 21/02* (2013.01); *A61B 5/0022* (2013.01); *A61B 5/742* (2013.01); *G06Q 10/06311* (2013.01)

(58) Field of Classification Search
None
See application file for complete search history.

(56) References Cited

U.S. PATENT DOCUMENTS

| | | | |
|---|---|---|---|
| 8,595,831 B2 * | 11/2013 | Skare ................. | G05B 23/0267 434/118 |
| 2011/0202490 A1 | 8/2011 | Gawlick | |
| 2014/0316804 A1 * | 10/2014 | Tran .................... | G06Q 10/1097 705/2 |
| 2014/0365390 A1 | 12/2014 | Braun | |

FOREIGN PATENT DOCUMENTS

TW 200744012 12/2007

* cited by examiner

*Primary Examiner* — Joseph Feild
*Assistant Examiner* — John Mortell
(74) *Attorney, Agent, or Firm* — Winston Hsu (57) ABSTRACT

A medical alert message handling method for a medical communication device is disclosed. The medical alert message handling method includes receiving a shift, a medical alert message classification configuration and a medical alert message priority configuration, receiving at least one medical alert message, filtering the medical alert message according to the shift to generate a personal alert message, displaying the personal alert message, filtering the medical alert message according to the medical alert message classification configuration and the medical alert message priority configuration, receiving a selection command to select one of the medical alert message, and noting a handling status and a handling problem of the selected medical alert message.

9 Claims, 12 Drawing Sheets

| Medical alert message | Priority |
|---|---|
| ECG lost | High |
| No pulse | High |
| High blood glucose | Medium |
| Tachycardia | Medium |
| ECG noise | Low |
| Circuit fault | Low |

MEDICAL ALERT MESSAGE PRE-CONFIGURATION AND MISSION HANDLING METHOD

CROSS REFERENCE TO RELATED APPLICATIONS

This application claims the benefit of U.S. Provisional Application No. 62/270,045 filed on Dec. 21, 2015, the contents of which are incorporated herein.

BACKGROUND OF THE INVENTION

1. Field of the Invention

The present invention is related to a medical alert message pre-setup and task assignment method, which can configure medical alert message in advance and can instantly assign and update tasks.

2. Description of the Prior Art

Medical apparatuses employed inwards, such as a physiological monitor, electrocardiogram machine and ventilator, usually have medical alert functions. Once a monitored value is abnormal, or the medical apparatus malfunctions, the medical apparatus outputs and sends a medical alert message to a nursing station of a hospital or a computer workstation of a monitoring center. As a result, when a duty staff of the nursing station or the monitoring center notices the medical alert message, the duty staff can immediately call a corresponding medical staff according to a shift, such that the medical staff can instantly go to the ward and handle the emergency.

According to the medical alert message handling procedure, a gateway of a clinical information system sends the medical alert messages via a cable network or a wireless network to a server, and the server stores the medical alert messages in a server database. In general, a terminal workstation is installed in the nursing station or the monitoring center, and the terminal workstation instantly monitors the medical alert messages via an intranet of the hospital.

However, since the medical staff has to look after multiple sickbeds at the same time, and each sickbed is usually equipped with more than two medical apparatuses, the medical alert message handling procedure cannot let the medical staff handle so many medical alert messages at the same time. In such a situation, some of the medical alert messages will not be timely handled, which means that the medical staff cannot reach the sickbed at the first time.

Therefore, the medical alert message handling procedure has to be improved, so as to respond to more medical alert messages.

SUMMARY OF THE INVENTION

It is therefore a primary objective of the claimed invention to provide a method capable of configuring medical alert messages in advance and temporarily assigning tasks.

The present invention discloses a medical alert message handling method for a medical communication device, which comprises receiving a shift, a medical alert message classification configuration and a medical alert message priority configuration; receiving at least one medical alert message; filtering the at least one medical alert message according to the shift, to generate a personal alert message; displaying the personal alert message; filtering the at least one medical alert message according to the medical alert message classification configuration and the medical alert message priority configuration; receiving a selection command to select one of the at least one medical alert message; and noting a handling status and a handling problem of the selected medical alert message.

The present invention further discloses a pre-setup method for configuring a medical communication device, which comprises receiving a shift, a medical alert message classification configuration and a medical alert message priority configuration; broadcasting the shift, the medical alert message classification configuration and the medical alert message priority configuration; and storing the shift, the medical alert message classification configuration and the medical alert message priority configuration.

The present invention further discloses a task handling method for a medical communication device, which comprises receiving at least one medical alert message; displaying the at least one medical alert message; receiving an assignment command; assigning one of the at least one medical alert message to a staff identification code according to the assignment command, to complete a task assignment; updating the assigned medical alert message according to the task assignment to generate an updated medical alert message; and broadcasting the updated medical alert message to another medical communication device.

The present invention further discloses a medical alert message handling method for a medical communication device, which comprises receiving at least one medical alert message; displaying the at least one medical alert message; receiving a selection command to select one of the at least one medical alert message; and noting a handling status and a handling problem of the selected medical alert message.

These and other objectives of the present invention will no doubt become obvious to those of ordinary skill in the art after reading the following detailed description of the preferred embodiment that is illustrated in the various figures and drawings.

DETAILED DESCRIPTION

Figure 1A:
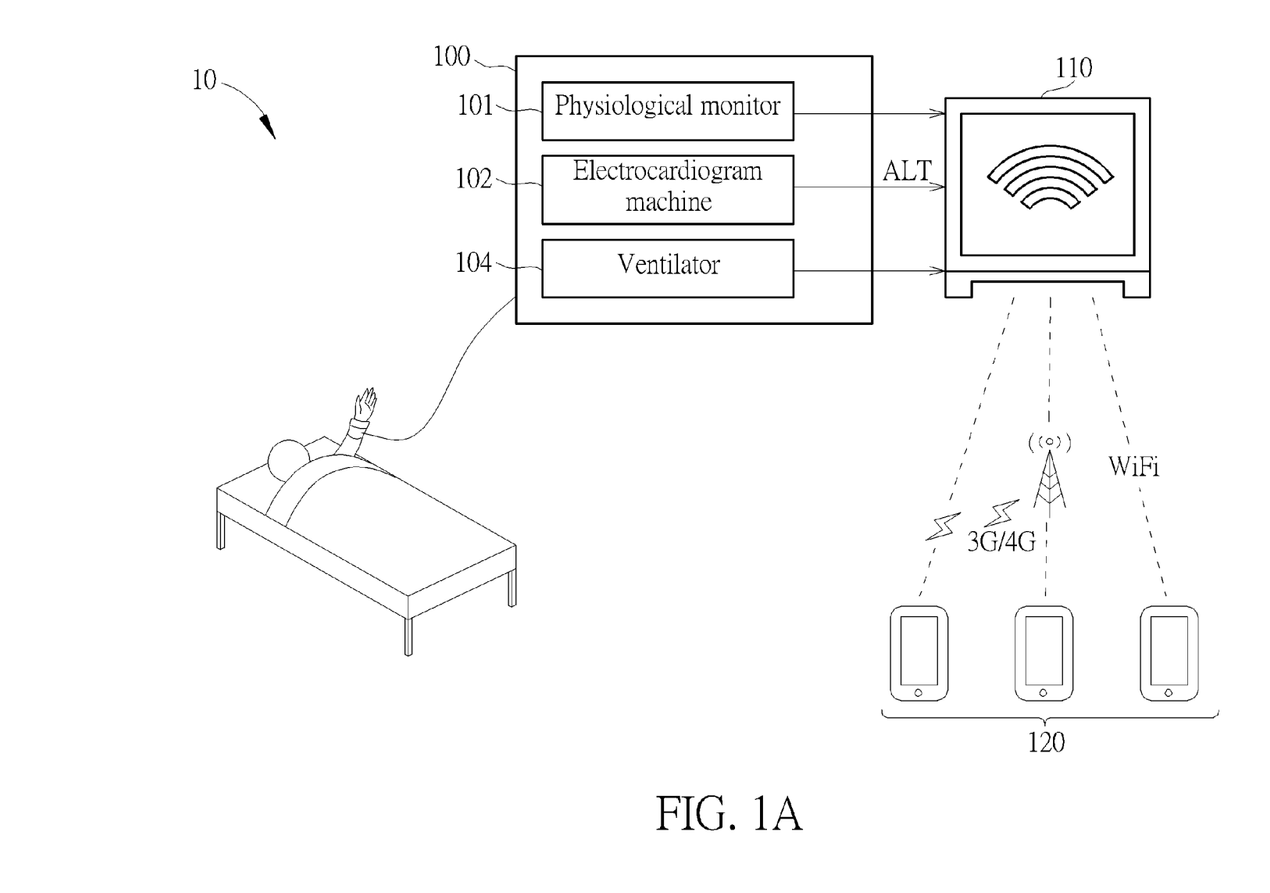
FIG. 1A is a schematic diagram of an information system according to an embodiment of the present invention.

Please refer to FIG. 1A, which is a schematic diagram of an information system 10 according to an embodiment of the present invention. The information system 10 includes a monitoring apparatus 100, a gateway 110 and multiple medical communication devices 120. The monitoring apparatus 100 is utilized for monitoring physiological values of a patient, and includes various medical sensing devices, such as a physiological monitor 101, an electrocardiogram machine 102 and a ventilator 104. The physiological values measured by the monitoring apparatus 100 are utilized for determining whether or not the monitoring apparatus 100 or the patient requires an urgent care. If the monitoring apparatus 100 or the patient requires the urgent care, the monitoring apparatus 100 generates a medical alert message ALT. The gateway 110 collects the medical alert message ALT, and sends the medical alert message ALT to the medical communication device 120 via a Wi-Fi (IEEE 802.11) network, a 3G or 4G network.

Figure 1B:
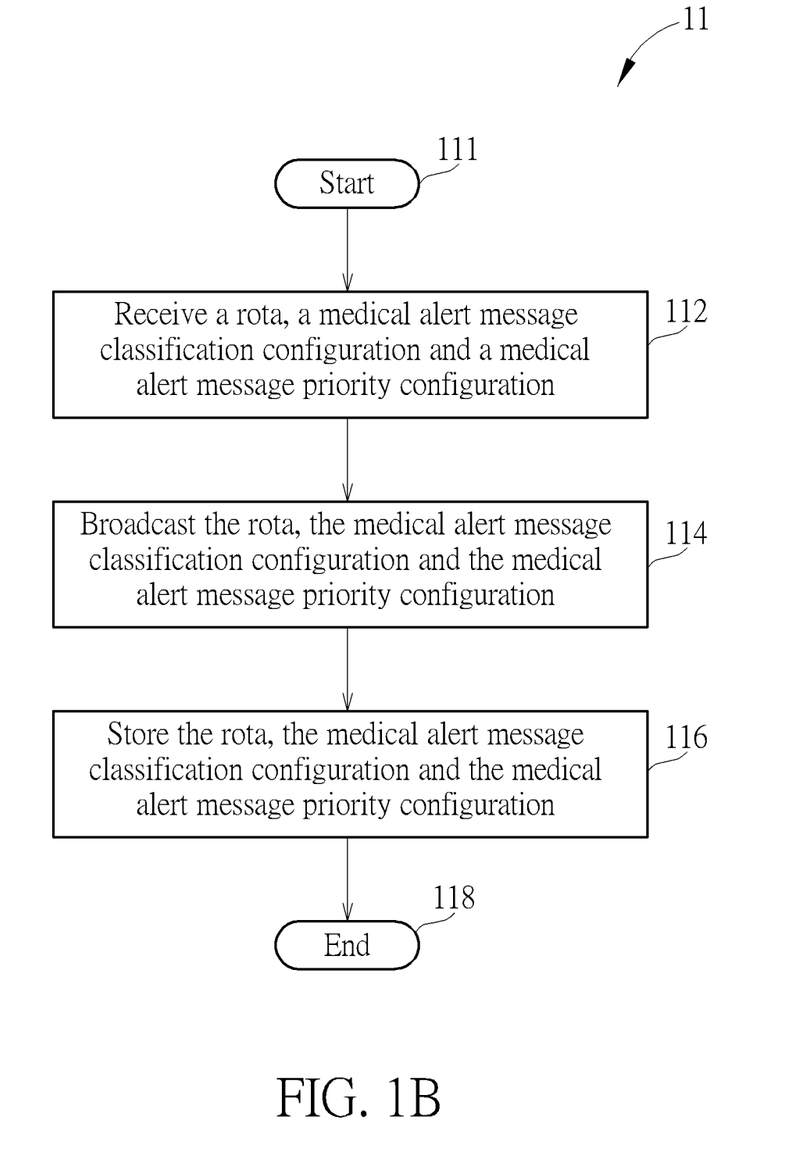
FIG. 1B is a flowchart of a pre-setup process according to an embodiment of the present invention.

Regarding operations of the medical communication device 120, please refer to FIG. 1B, which is a flowchart of a pre-setup process 11 according to an embodiment of the present invention. The pre-setup process 11 is utilized for configuring the medical communication device 120 before the medical communication device 120 is on duty, and includes the following steps:

Step 111: Start.
Step 112: Receive a shift, a medical alert message classification configuration and a medical alert message priority configuration.
Step 114: Broadcast the shift, the medical alert message classification configuration and the medical alert message priority configuration.
Step 116: Store the shift, the medical alert message classification configuration and the medical alert message priority configuration.
Step 118: End.

Figure 1C:
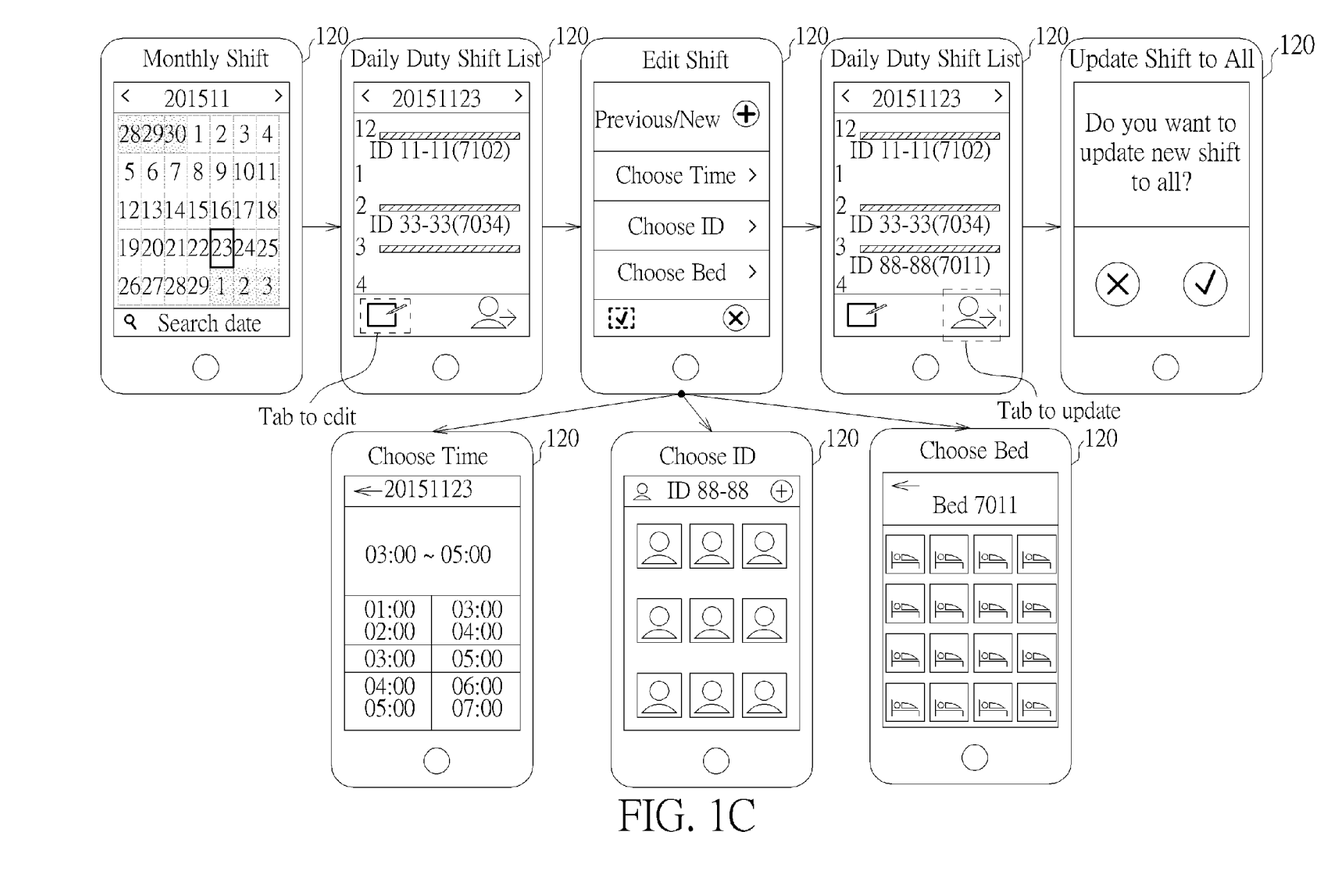
FIG. 1C is a schematic diagram of a user interface of a medical communication device of FIG. 1A while updating a shift.

The medical communication device 120 is designed for nursing staffs, which are classified into a nursing supervisor and common nursing staffs. The nursing supervisor has higher authority for operating the medical communication device 120 than the common nursing staffs, and can configure the medical communication device 120 based on the pre-setup process 11 before on duty. After the medical communication device 120 receives the shift, the medical alert message classification configuration and the medical alert message priority configuration inputted by the nursing supervisor, the medical communication device 120 broadcasts the shift, the medical alert message classification configuration and the medical alert message priority configuration to other medical communication devices 120. As a result, all of the medical communication devices 120 can receive the latest shift, the latest medical alert message classification configuration and the latest medical alert message priority configuration before on duty. For example, please refer to FIG. 1C, which is a schematic diagram of a user interface of the medical communication device 120 while updating the shift.

Figure 1D:
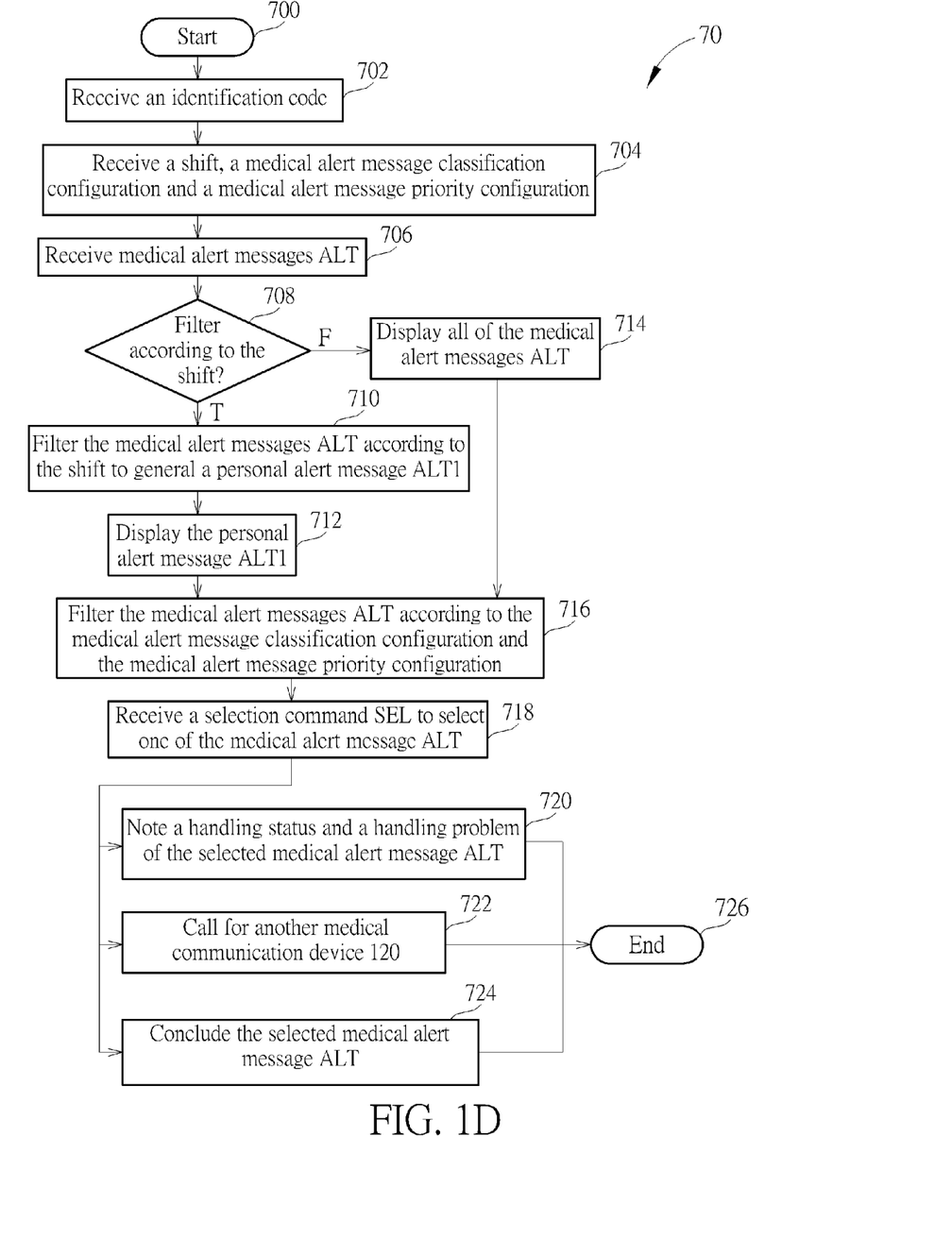
FIG. 1D is a flowchart of a medical alert message handling process according to an embodiment of the present invention.

Regarding operations that the medical communication device 120 is on duty, please refer to FIG. 1D, which is a flowchart of a medical alert message handling process 70 according to an embodiment of the present invention. The medical alert message handling process 70 includes the following steps:

Step 700: Start.
Step 702: Receive an identification code.
Step 704: Receive a shift, a medical alert message classification configuration and a medical alert message priority configuration.
Step 706: Receive medical alert messages ALT.
Step 708: If the shift is received, proceed to Step 710; else, proceed to Step 714.
Step 710: Filter the medical alert messages ALT according to the shift to general a personal alert message ALT1.
Step 712: Display the personal alert message ALT1. Proceed to Step 716.
Step 714: Display all of the medical alert messages ALT.
Step 716: Filter the medical alert messages ALT according to the medical alert message classification configuration and the medical alert message priority configuration.
Step 718: Receive a selection command SEL to select one of the medical alert message ALT.
Step 720: Note a handling status and a handling problem of the selected medical alert message ALT. Proceed to Step 726.
Step 722: Call for another medical communication device 120. Proceed to Step 726.
Step 724: Conclude the selected medical alert message ALT. Proceed to Step 726.
Step 726: End.

Figure 1E:
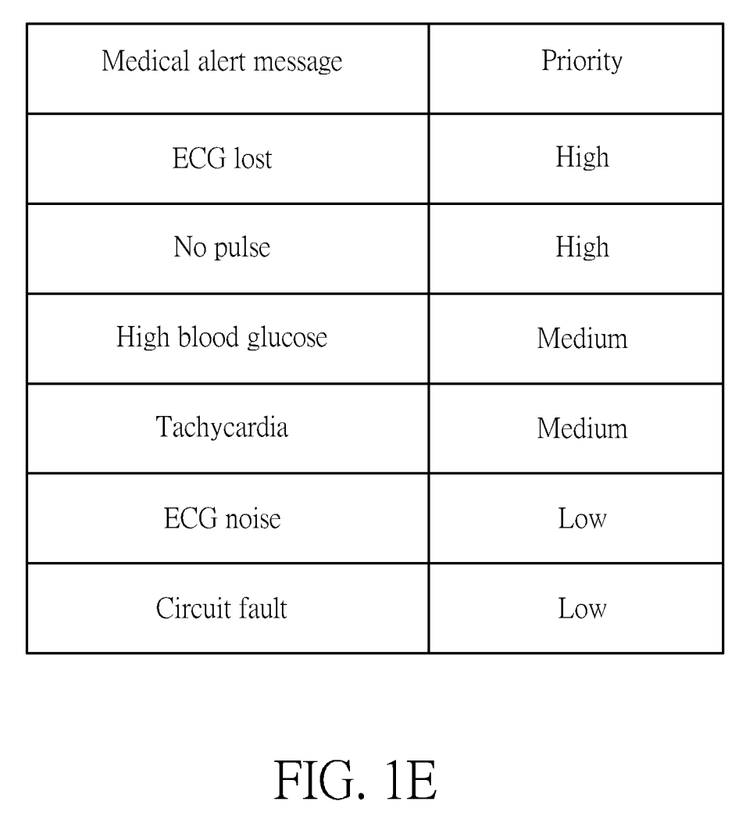
FIG. 1E is a schematic diagram illustrating priority of medical alert messages.

Other than the classifications of the medical alert messages, the medical alert messages ALT may also be filtered based on the priory configuration. Please refer to FIG. 1E, which is a schematic diagram illustrating priorities of the medical alert messages ALT. For example, according to the priority table of FIG. 1E, if the medical communication device 120 simultaneously receives two medical alert messages "sickbed 1: electrocardiogram lost" and "sickbed 2: circuit fault" at AM 10:00, and receives another medical alert message "sickbed 5: high blood glucose", the medical communication device 120 filters the medical alert messages ALT according to Step 716, and reorders the medical alert messages ALT, such that "sickbed 1: electrocardiogram lost" would be handled firstly, "sickbed 5: high blood glucose" would be handled secondly and "sickbed 2: circuit fault" would be handled thirdly. As a result, the medical communication device 120 can present the most urgent medical alert message ALT to the nursing staff, and the nursing staff no longer has to manually order the medical alert messages ALT.

Figure 2:
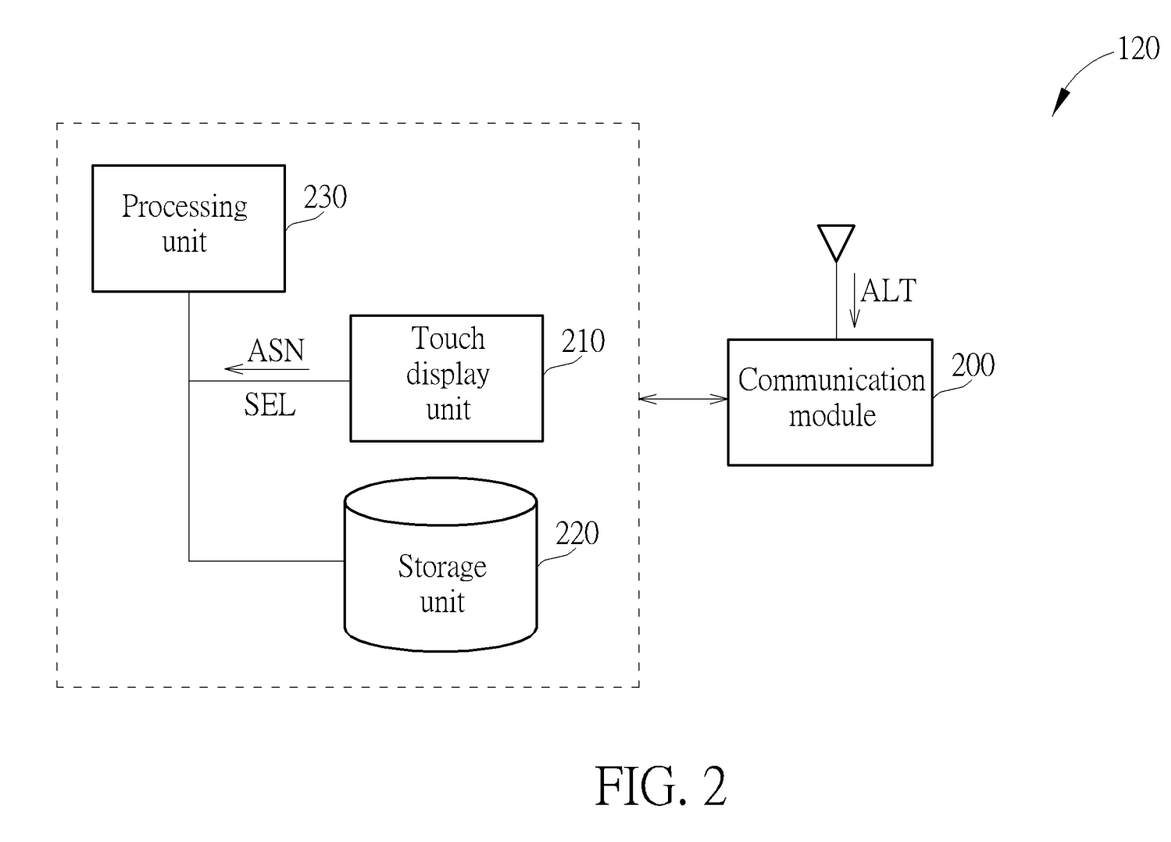
FIG. 2 is a schematic diagram of a medical communication device of the information system of FIG. 1A.

Regarding implementation of the pre-setup process 11 and the medical alert message handling process 70, please refer to FIG. 2, which is a schematic diagram of the medical communication device 120. The medical communication device 120 includes a communication module 200, a touch display unit 210, a storage unit 220 and a processing unit 230. The communication module 200 is utilized for receiving the medical alert messages ALT. The touch display unit 210 is utilized for displaying the medical alert messages ALT and receiving the selection command SEL or an assignment command ASN. The storage unit 220 is utilized for storing a program code recording instructions of the pre-setup process 11 and the medical alert message handling process 70. Finally, the processing unit 230 executes the instructions compiled in the program code.

In short, in order to timely respond to numerous medical alert messages ALT, the information system 10 applies an instant task assignment and reporting mechanism. As such, each of the nursing staffs involved in the information system 10 can instantly acquire the latest handling status of the medical alert messages ALT, so as to immediately respond to the medical alert messages ALT.

Figure 3A:
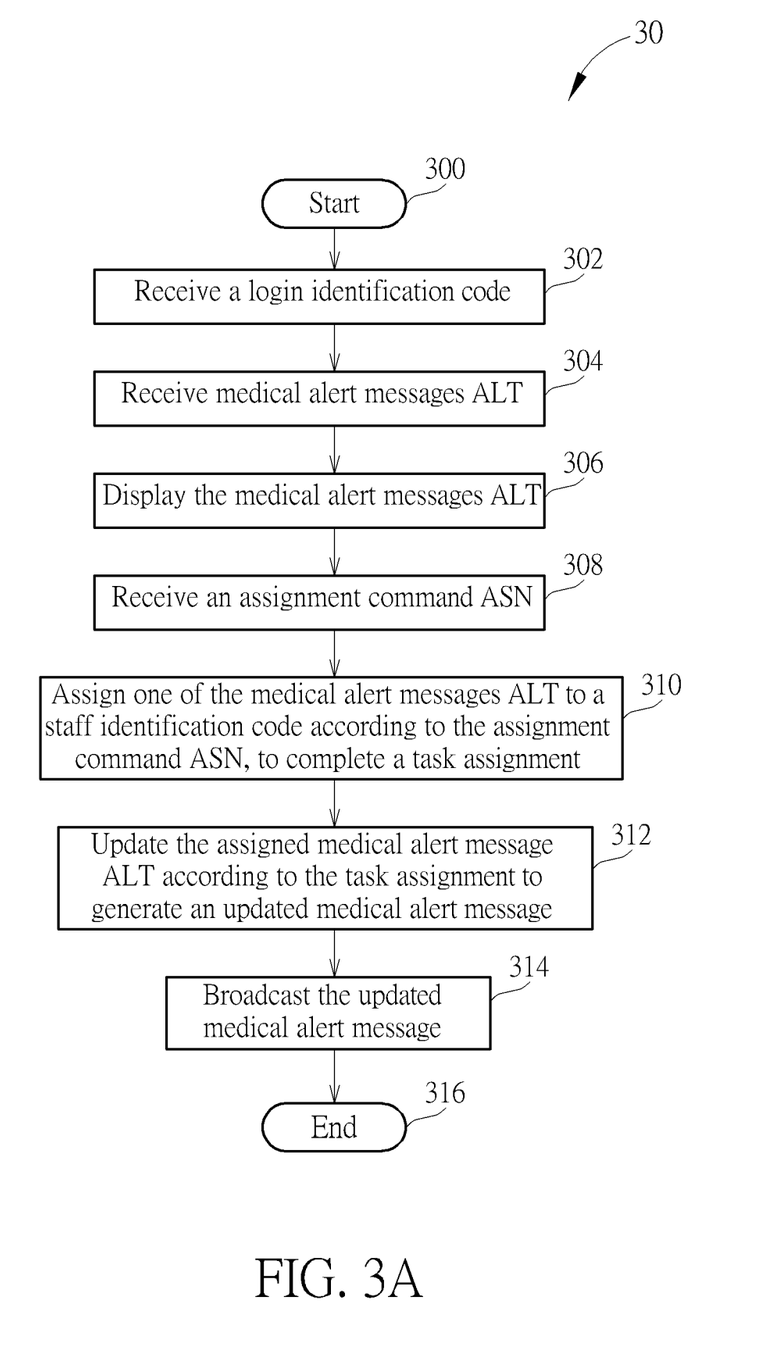
FIG. 3A is a flowchart of a temporary task assignment process according to an embodiment of the present invention.

However, in medical practices, when one of the medical alert messages ALT is assigned to a nurse A according to the shift, the nurse A may be busy and cannot timely respond to the assigned medical alert message ALT. Also, if other nursing staffs do not voluntarily take over the assigned medical alert message ALT via their respective medical communication devices 120, the nursing supervisor can temporarily reassign the medical alert message ALT to one of the nursing staffs other than the nurse A by commanding the medical communication device 120. Specifically, the above operations can be summarized into a temporary task assignment process 30, as illustrated in FIG. 3A. The temporary task assignment process 30 includes the following steps:

Step 300: Start.
Step 302: Receive a login identification code.
Step 304: Receive medical alert messages ALT.
Step 306: Display the medical alert messages ALT.
Step 308: Receive an assignment command ASN.
Step 310: Assign one of the medical alert messages ALT to a staff identification code according to the assignment command ASN, to complete a task assignment.
Step 312: Update the assigned medical alert message ALT according to the task assignment to generate an updated medical alert message.
Step 314: Broadcast the updated medical alert message.
Step 316: End.

Figure 3B:
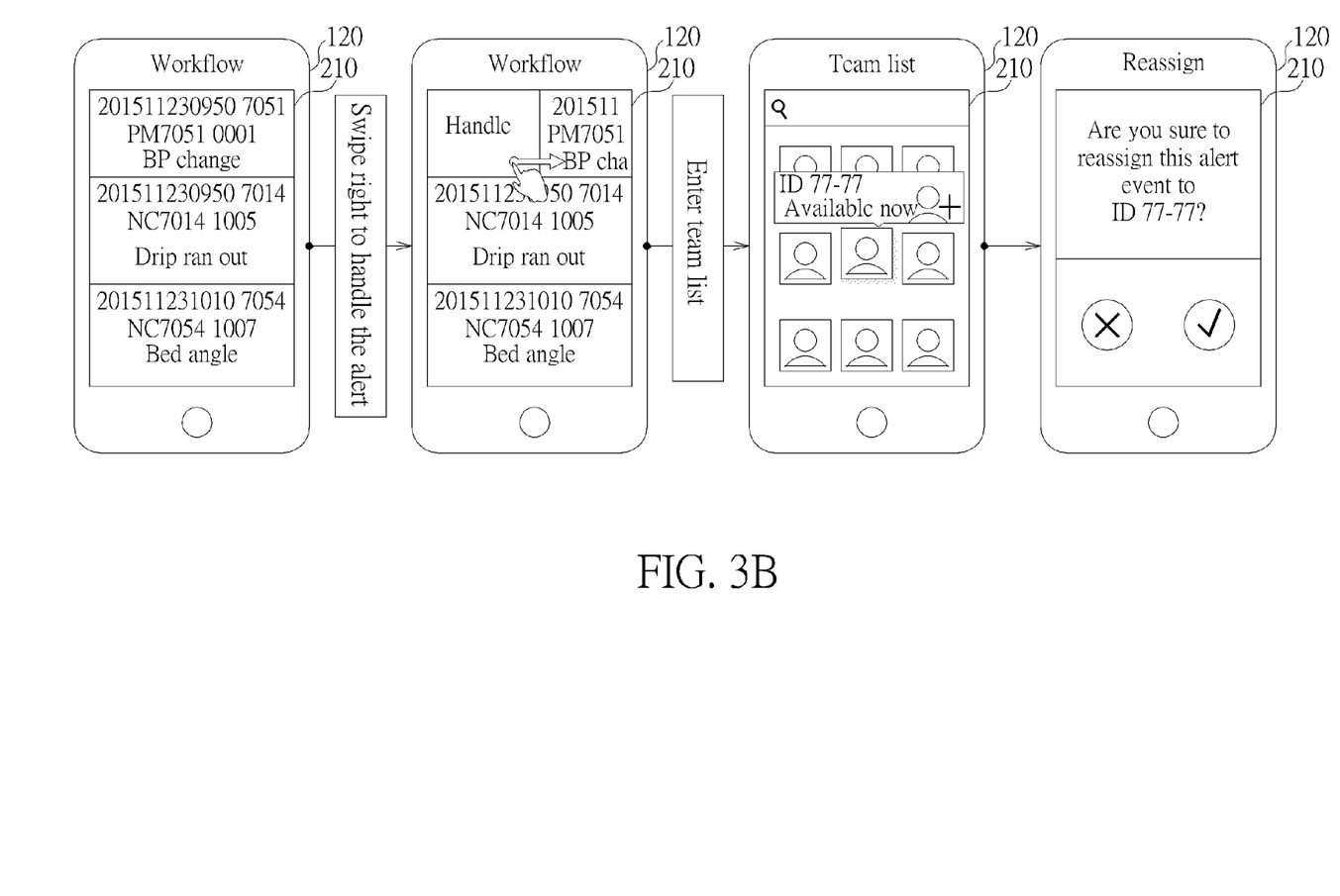
FIG. 3B is a schematic diagram of a task assignment process of the medical communication device of FIG. 1A.

For example, please refer to FIG. 3B, which is a schematic diagram of a task assignment process of the medical communication device 120 and the touch display unit 210. After the medical communication device 120 receives the medical alert messages ALT sent from the gateway 110, the touch display unit 210 displays all of the medical alert messages ALT. An operator of the medical communication device 120, such as a nursing supervisor, inputs the assignment command ASN via the touch display unit 210, so as to assign one of the medical alert messages ALT to the staff identification code. In FIG. 3B, the nursing supervisor assigns the medical alert message "blood pressure change" to the staff identification code "77-77".

Figure 4A:
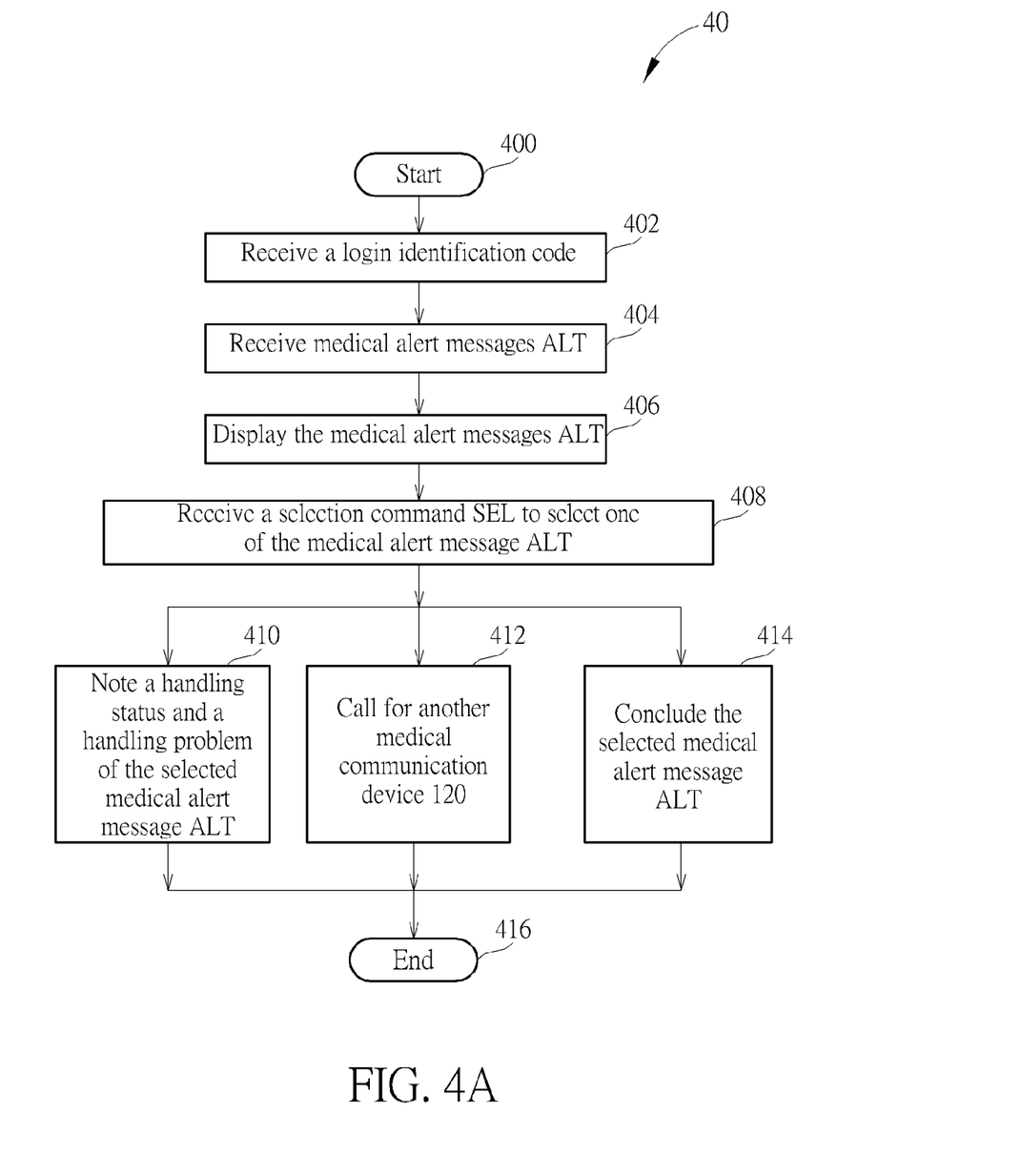
FIG. 4A is a flowchart of a task handling process according to an embodiment of the present invention.

Other than the supervisor assignment, when the medical communication device 120 does not receive the shift, the medical alert message classification configuration and the medical alert message priority configuration before on duty, the medical alert messages ALT can be voluntarily undertaken by an on-duty nursing staff. Specifically, the above operations can be summarized into a medical alert message handling process 40, as shown in FIG. 4A. The medical alert message handling process 40 includes the following steps:

Step 400: Start.
Step 402: Receive a login identification code.
Step 404: Receive medical alert messages ALT.
Step 406: Display the medical alert messages ALT.
Step 408: Receive a selection command SEL to select one of the medical alert message ALT.
Step 410: Note a handling status and a handling problem of the selected medical alert message ALT. Proceed to Step 416.
Step 412: Call for another medical communication device 120. Proceed to Step 416.
Step 414: Conclude the selected medical alert message ALT.
Step 416: End.

Figure 4B:
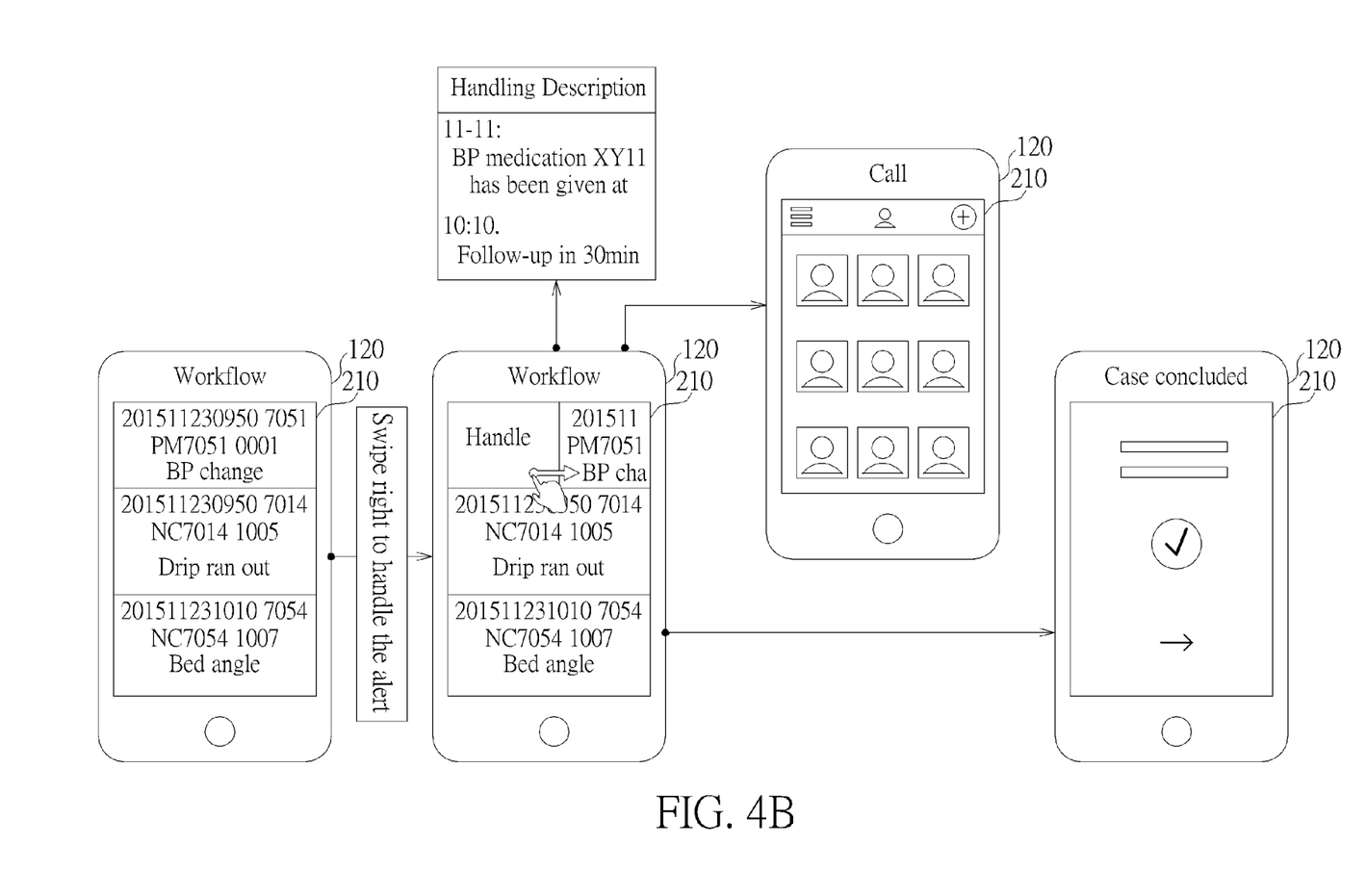
FIG. 4B is a schematic diagram of an embodiment of the task handling process of FIG. 4A.

For example, please refer to FIG. 4B, which is a schematic diagram of an embodiment of the medical alert message handling process 40. In FIG. 4B, an operator inputs the selection command SEL to the medical alert message "blood pressure change" via the touch display unit 210. After "blood pressure change" is selected, the operator has three options. The first option is to note the handling status of "blood pressure change" as "BP medication XY11 has been given at 10:10. Follow-up in 30 min." The second option is to call for another medical communication device 120 to search for help from other nursing staffs. The third option is to conclude the medical alert message "blood pressure change".

Note that, the communication module 200 has to transmit the updated handling status, e.g. "BP medication XY11 has been given at 10:10. Follow-up in 30 min" shown in FIG. 4B, to all other medical communication devices 120, such that all on-duty operators involved in the information system 10 can acquire the latest status for all medical alert messages ALT. The medical communication devices 120 can communicate with each other via a Wi-Fi network, a 3G or 4G network or a pear-to-peer network. In addition, the medical communication devices 120 can acquire the latest message statuses by sharing files with each other.

Figure 5:
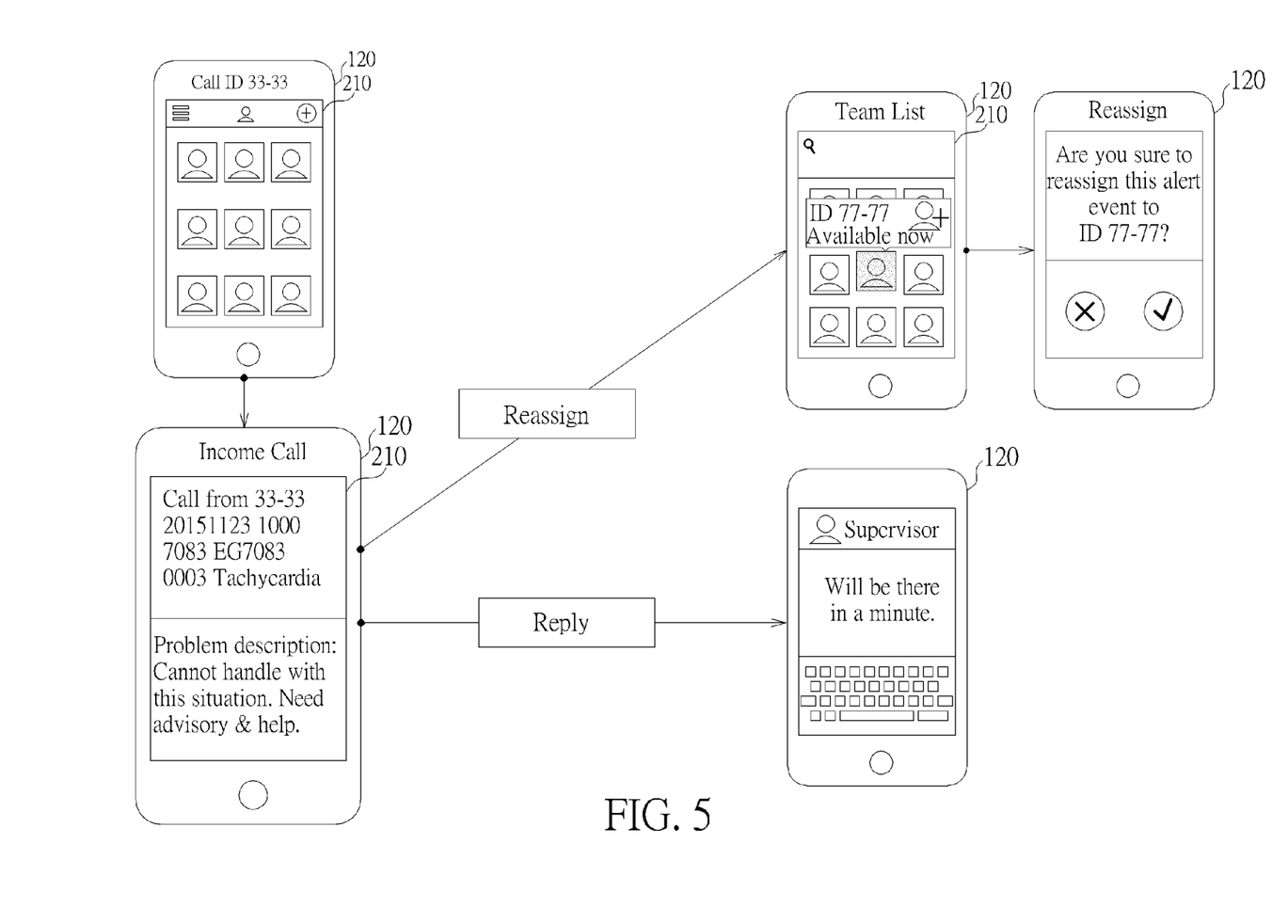
FIG. 5 is a schematic diagram that the medical communication device of FIG. 1A replies to a call from another medical communication device.

Due to capability or time limit, the operator may not be able to handle the assigned medical alert message ALT. Accordingly, other than updating the handling status, the medical communication device 120 could further record and broadcast the handling problem of the assigned medical alert message ALT, such as "Cannot handle with this situation. Need advisory & help" as shown in FIG. 5. That is, the handling status and the handling problem can both be updated. On the other hand, when the operator (common nursing staff) of the medical communication device 120 calls for the operator (nursing supervisor) of another medical communication device 120 to search for help, the medical communication device 120 allows the nursing supervisor replying to the common nursing staff by text or reassigning the medical alert message ALT to another staff identification code, such as "77-77" shown in FIG. 5.

Figure 4C:
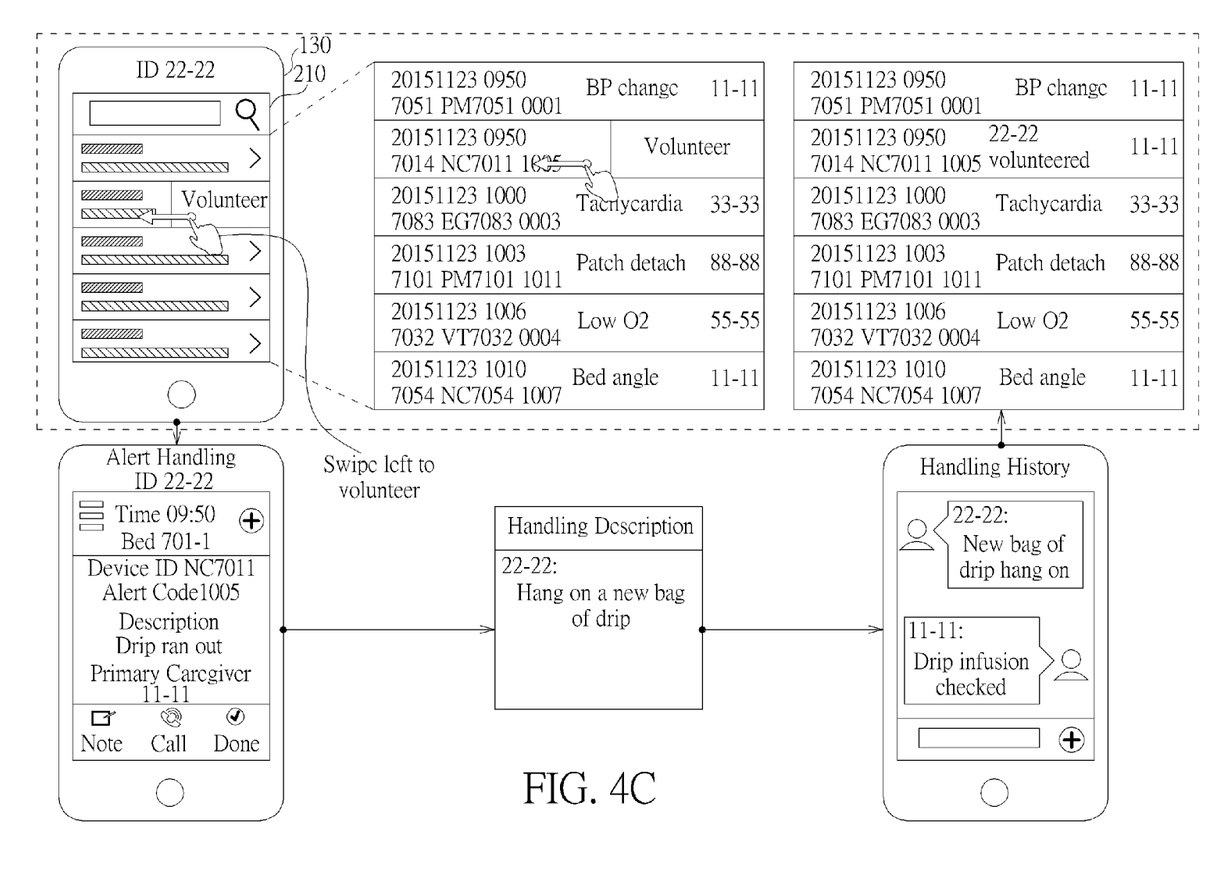
FIG. 4C is a schematic diagram that a volunteer handles a medical alert message by the medical communication device of FIG. 1A.

In detail, please refer to FIG. 4C, which is a schematic diagram of the user interface of the medical communication device 120 when the common nursing staff voluntarily handles an unassigned medical alert message ALT. In FIG. 4C, an operator with a login identification code "22-22" voluntarily handles the medical alert message numbered by "NC7011", which is originally assigned to the operator with the login identification code "11-11". Since the operator is allowed to voluntarily handle the medical alert messages ALT, an important medical alert message ALT would be timely undertaken by a free nursing staff when the assigned nursing staff is busy, so as to improve efficiency and flexibility of the information system 10.

Furthermore, to avoid a case that nobody responds to one of medical alert messages ALT for a long period, the medical communication device 120 can monitor response times of all the assigned medical alert messages ALT. If the response time of one of the medical alert messages ALT exceeds a predetermined threshold, the information system 10 may remind all the involved operators via sounds or eye-catching remarks to handle the medical alert message ALT quickly.

To sum up, in order to timely respond to numerous medical alert messages, the present invention utilizes an instant task assignment and reporting mechanism, such that all operators involved in the information system can acquire the latest statuses of all the medical alert messages.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A medical alert message handling method for a medical communication device, the medical alert message handling method comprising:
    executing a pre-setup method, which comprises receiving a shift, a medical alert message classification configuration and a medical alert message priority configuration;
    receiving a plurality of medical alert messages collected by at least one gateway;
    displaying at least one first medical alert message pre-assigned to a first staff according to a first display selection, wherein the first display selection indicates that the plurality of medical alert messages is filtered according to the shift to generate the at least one first medical alert message, comprising:
        sorting the at least one first medical alert message according to the medical alert message classification configuration and the medical alert message priority configuration; or
    displaying the plurality of medical alert messages according to a second display selection, wherein the second display selection indicates that the plurality of medical alert messages is not filtered according to the shift, comprising:
        sorting the plurality of medical alert messages according to the medical alert message classification configuration and the medical alert message priority configuration;
    receiving a selection command to select one of the at least one first medical alert message pre-assigned to the first staff or one of the plurality of medical alert messages pre-assigned to a second staff to generate a selected medical alert message; and
    executing a function, which comprises:
        noting a handling status, a handling problem, calling for a care communication device and concluding the selected medical alert message; and
        updating and broadcasting the selected medical alert message to at least one other medical communication device.

2. The medical alert message handling method of claim 1, wherein the medical communication device broadcasts the shift, the medical alert message classification configuration, the medical alert message priority configuration and the selected medical alert message to at least one other medical communication device via a Wi-Fi network, a 3G network or a 4G network.

3. A task handling method for a medical communication device, comprising:
    receiving a plurality of medical alert messages;
    displaying at least one first medical alert message pre-assigned to a first staff according to a first display selection, wherein the first display selection indicates that the plurality of medical alert messages is filtered according to a shift to generate the at least one first medical alert message; or
    displaying the plurality of medical alert messages according to a second display selection, wherein the second display selection indicates that the plurality of medical alert messages is not filtered according to the shift;
    receiving an assignment command;
    assigning one of the at least one first medical alert message pre-assigned to the first staff or one of the plurality of medical alert messages pre-assigned to a second staff to a staff identification code according to the assignment command, to complete a task assignment;
    updating the one of the at least one first medical alert message pre-assigned to the first staff or the one of the plurality of medical alert messages pre-assigned to the second staff according to the task assignment to generate an updated medical alert message; and
    broadcasting the updated medical alert message to another medical communication device.

4. The task handling method of claim 3, wherein the medical communication device receives the plurality of medical alert messages and broadcasts the updated medical alert message via a Wi-Fi network, a 3G network or a 4G network.

5. A medical alert message handling method for a medical communication device, the medical alert message handling method comprising:
    receiving a plurality of medical alert messages collected by at least one gateway;
    displaying at least one first medical alert message pre-assigned to a first staff according to a first display selection, wherein the first display selection indicates that the plurality of medical alert messages is filtered according to a shift to generate the at least one first medical alert message; or
    displaying the plurality of medical alert messages according to a second display selection, wherein the second display selection indicates that the plurality of medical alert messages is not filtered according to the shift;
    receiving a selection command to select one of the at least one first medical alert message pre-assigned to the first staff or one of the plurality of medical alert messages pre-assigned to a second staff to generate a selected medical alert message; and
    noting a handling status and a handling problem of the selected medical alert message.

6. The medical alert message handling method of claim 5, further comprising:
    calling for a care communication device.

7. The medical alert message handling method of claim 5, further comprising:
    concluding the selected medical alert message.

8. The medical alert message handling method of claim 5, wherein the medical communication device received the plurality of medical alert messages via a Wi-Fi network, a 3G network or a 4G network.

9. The medical alert message handling method of claim 1, further comprising:
    receiving an assignment command; and
    assigning one of the at least one first medical alert message pre-assigned to the first staff or one of the plurality of medical alert messages pre-assigned to the second staff to a staff identification code according to the assignment command, to complete a task assignment.

* * * * *